(12) United States Patent
Panton, III et al.

(10) Patent No.: US 12,168,095 B2
(45) Date of Patent: Dec. 17, 2024

(54) RESUSCITATION TRAINING DEVICE

(71) Applicant: Water Safety Products, Inc., Palm Bay, FL (US)

(72) Inventors: George S. Panton, III, Melbourne Beach, FL (US); Alex Stenzler, Long Beach, CA (US); Joanne Creighton, Huntington Beach, CA (US)

(73) Assignee: Water Safety Products, Inc.

( * ) Notice: Subject to any disclaimer, the term of this patent is extended or adjusted under 35 U.S.C. 154(b) by 836 days.

(21) Appl. No.: 17/150,032

(22) Filed: Jan. 15, 2021

(65) Prior Publication Data

US 2021/0220584 A1    Jul. 22, 2021

Related U.S. Application Data

(60) Provisional application No. 62/962,605, filed on Jan. 17, 2020.

(51) Int. Cl.
*A61M 16/00* (2006.01)
*A61M 16/04* (2006.01)
*A61M 16/08* (2006.01)
*A61M 16/20* (2006.01)
*G09B 23/28* (2006.01)

(52) U.S. Cl.
CPC ...... *A61M 16/0048* (2013.01); *A61M 16/047* (2013.01); *A61M 16/0833* (2014.02); *A61M 16/20* (2013.01); *G09B 23/288* (2013.01)

(58) Field of Classification Search
CPC .............. A61M 16/00; A61M 16/0048; A61M 16/047; A61M 16/04; A61M 16/0833; A61M 16/08; A61M 16/20; G09B 23/28; G09B 23/288
See application file for complete search history.

(56) References Cited

U.S. PATENT DOCUMENTS

| | | | | |
|---|---|---|---|---|
| 5,562,093 A | * | 10/1996 | Gerson | A61M 16/0048 128/202.28 |
| 5,584,288 A | * | 12/1996 | Baldwin | A61M 16/0048 128/202.28 |
| 2017/0294145 A1 | * | 10/2017 | Kwon | G01L 1/16 |
| 2019/0217029 A1 | * | 7/2019 | Lawrence | A61M 16/0048 |
| 2019/0362653 A1 | * | 11/2019 | Zhao | G09B 23/288 |

FOREIGN PATENT DOCUMENTS

KR    20110008408 U    * 11/2019 ............ G09B 23/288

* cited by examiner

*Primary Examiner* — Jay Trent Liddle
*Assistant Examiner* — Alyssa N Brandley
(74) *Attorney, Agent, or Firm* — Riverside Law LLP (57) ABSTRACT

A split passageway resuscitation training device is described. Embodiments of the split passageway resuscitation training device can be implemented with a cardiopulmonary resuscitation (CPR) mask, a CPR valve (with or without a mask), or a CPR resuscitation bag. The split passageway resuscitation training device can allow a simulated rescuer and a simulated victim to use a CPR mask. For instance, the split passageway resuscitation training device can allow the training rescuer to practice exhaling into the mask without the "live" victim having to inhale the rescuer's breaths. The split passageway resuscitation training device also allows the victim to breathe through a different passageway of the device while wearing the mask.

18 Claims, 5 Drawing Sheets

RESUSCITATION TRAINING DEVICE

CROSS-REFERENCE TO RELATED APPLICATIONS

This application claims priority to U.S. Provisional Patent Application No. 62/962,605, filed Jan. 17, 2020, the contents of which are incorporated by reference herein in its entirety.

BACKGROUND

Resuscitation of a victim who is not breathing requires artificial respiration that can be provided by mouth-to-mouth or direct mouth-to-mask from a rescuer, which exposes the rescuer to the victim's exhalation. Resuscitation devices have also been designed to protect the rescuer so that they do not inhale the air from the victim. There are devices that contain one-way valves that enable the rescuer to blow the air from their lungs into the victim's lungs but direct the victim's exhalation into the room. There are also resuscitation bags with valves that when the bag is filled with room air, it can be squeezed to push the air into the victim's lungs while protecting the bag from the victim's exhalation.

When rescuers are being trained in this technique, they are usually partnered with another rescuer that acts as the victim. The trainee places a mask on the "victim's" face and verbally simulates of the act of breathing into the mask or valve. Actually breathing into the mask would expose each partner to the other's exhalation, and without the risk of death without actual resuscitation in consideration, rescuers are unwilling to inhale the other rescuer's breath.

To make the training more realistic, a device that allows the rescuer to place a mask or a mask and valve on a live victim and breathe into the device without exposing the victim to their exhalation, while at the same time allow the victim to spontaneously breathe with the mask in place but without inhaling the exhalation of the rescuer is needed.

SUMMARY OF THE INVENTION

In one aspect, the present invention provides a split passageway resuscitation training device comprising: a housing having a first portion and a second portion; wherein the first portion defines a first passageway extending between an upper first opening and a second opening positioned at an end of a laterally extending snout; wherein the second portion defines a second passageway extending between a plurality of side openings and a lower opening; and wherein the first portion of the housing is adapted to interface with a source of resuscitation air and the second portion of the housing is adapted to interface with a cardiopulmonary resuscitation mask.

In one embodiment, the first opening of the first portion is a circular opening having a diameter between about 21 and 23 millimeters, and the second opening is located approximate to a middle portion of the housing. In one embodiment, the second portion comprises at least two legs, the at least two legs defining a tubular space having an outer diameter between about 21 and 23 millimeters, and wherein each leg comprises an exterior physical stop extending past the outer diameter, such that each physical stop limits a depth of insertion of the at least two legs into a cardiopulmonary resuscitation mask tube and exposes the plurality of side openings. In one embodiment, the tubular space comprises an inner diameter between about 14 and 16 millimeters.

In one embodiment, the first passageway is configured to channel a fluid entering from the first opening to exit from the second opening and to channel a fluid entering from the second opening to exit from the first opening. In one embodiment, the second passageway is configured to channel a fluid entering from the plurality of side openings to exit from the lower opening and to channel a fluid entering from the lower opening to exit from the plurality of side openings.

In one embodiment, the device further comprises an elastic balloon-like receptacle removably attached to the second opening of the first portion, wherein the receptacle is configured to collect a fluid flowing into the first opening of the first portion and to return the fluid to the first opening when a pressure at the second opening is greater than a pressure at the first opening. In one embodiment, the snout is removably attached to the housing.

In another aspect, the present invention provides a split passageway resuscitation training device comprising: a housing having a first portion and a second portion; wherein the first portion defines a first passageway extending between an upper first opening and a second opening positioned at an end of a laterally extending snout; wherein the second portion defines a second passageway extending between a plurality of side openings and a lower opening; and wherein the first portion of the housing is adapted to interface with a source of resuscitation air and the second portion of the housing is adapted to interface with an endotracheal tube.

In one embodiment, the first opening of the first portion is a circular opening having a diameter between about 21 and 23 millimeters, and the second opening is located approximate to a middle portion of the housing. In one embodiment, the second portion comprises at least two legs, the at least two legs defining a tubular space having an outer diameter between about 21 and 23 millimeters, and wherein each leg comprises an exterior physical stop extending past the outer diameter, such that each physical stop limits a depth of insertion of the at least two legs into an endotracheal tube and exposes the plurality of side openings. In one embodiment, the tubular space comprises an inner diameter between about 14 and 16 millimeters.

In one embodiment, the first passageway is configured to channel a fluid entering from the first opening to exit from the second opening and to channel a fluid entering from the second opening to exit from the first opening. In one embodiment, the second passageway is configured to channel a fluid entering from the plurality of side openings to exit from the lower opening and to channel a fluid entering from the lower opening to exit from the plurality of side openings.

In one embodiment, the device further comprises an elastic balloon-like receptacle removably attached to the second opening of the first portion, wherein the receptacle is configured to collect a fluid flowing into the first opening of the first portion and to return the fluid to the first opening when a pressure at the second opening is greater than a pressure at the first opening. In one embodiment, the snout is removably attached to the housing.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

DETAILED DESCRIPTION

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiments and are not necessarily intended to be construed as limiting.

Embodiments of the present invention include a split passageway resuscitation training device that allows a user to practice cardiopulmonary resuscitation (CPR) on a live person with a CPR mask. The split passageway resuscitation training device can allow a user working as a rescuer to practice giving breaths to another person acting as a "victim" without the victim inhaling the rescuer's exhaled breath and while allowing said rescuer to continue resuscitation training normally while the victim is wearing a CPR mask.

Generally, the split passageway resuscitation training device can include a housing having a first passageway and a second passageway. An opening can be located on one end of the housing as an interface with a source of resuscitation air for the first passageway. The first passageway can end in an opening on the side of the housing proximate a middle of the housing. The split passageway resuscitation training device's second passageway's first opening can be located on the opposite end of the housing to the opening of the first passageway. The second passageway's first opening can be created by legs forming a circular form that can be sized to be implemented with currently available CPR masks or endotracheal tubes. In one embodiment, the split passageway resuscitation training device can include a protruding snout at the second opening of the first passageway to accommodate an elastic balloon to help simulate lung inflation while performing CPR.

In a first embodiment, a split passageway resuscitation training device can be implemented to divert a rescuer's breath away from a CPR mask and couple to a CPR mask whereby a victim breathes through a separate pathway. The first embodiment split passageway resuscitation training device can allow a simulate rescuer and a simulated victim to breathe via different passageways of the device.

In a second embodiment, a split passageway resuscitation training device can be implemented to couple to a CPR mask and work in conjunction with a one-way CPR. The second embodiment split passageway resuscitation training device can allow simulated victim to breathe in via a separate passageway of the device and exhale normally through the CPR mask. Similar to the first embodiment, a simulated rescuer may practice giving breaths to the simulated victim through a CPR valve attached to the first passageway of the device with their air diverted from the CPR mask.

When using a typical CPR mask, air is administered to a patient (or victim) when a rescuer exhales into the mask applied to the victim or through a one-way valve that allows the air to pass to the patient. As can be appreciated, there would be no difficulty when practicing with a dummy that is not breathing, but would not be practical when practicing with a live person. More specifically, the live victim would need a way to breathe without inhaling the exhaled air of the rescuer and the victim would need to synchronize their breathing with the rescuer if inhaling the air was not an objection. Both the first and the second embodiment split passageway resuscitation training device can be implemented to allow two live persons to practice with a CPR mask with or without having a one-way valve.

In one embodiment, the split passageway resuscitation training device comprises a housing having a first portion and a second portion, the housing including a first passageway including a first opening and a second opening with a snout, the first passageway being located within the first portion of the housing; a second passageway being located substantially within the second portion of the housing; wherein the first portion of the housing is adapted to interface with a source of resuscitation air and the second portion of the housing is adapted to interface with a cardio-pulmonary resuscitation mask. The split passageway resuscitation training device wherein an elastic balloon like receptacle can be attached to the second opening snout to collect the rescuer's air flowing from the first opening, and return it to the first opening when the pressure at the second opening is greater than the pressure at the first opening.

Embodiments of the split passageway resuscitation training device can allow a simulated rescuer to practice blowing into a CPR mask to give rescue breaths without breathing into a victim who is simulating a patient requiring respiration support. With both the first and second embodiments of the split passageway resuscitation training device, each person has their own airway through which they are able to breathe. With the first embodiment split passageway resuscitation training device, the device is attached to the CPR mask alone. With the second embodiment split passageway resuscitation training device, the device can attach to a CPR mask and a one-way valve can be attached to the first passageway of the split passageway resuscitation training device. Of note, this may allow the person wearing the CPR mask to breathe through the mask the same way they would without the device attached. Since the device has two separate passageways (or airways), the device can still allow the rescuer to practice blowing into the device without breathing into the person wearing the CPR mask.

In one embodiment of the split passageway resuscitation training device can allow a simulated rescuer to practice giving breaths in a more realistic manner allowing the simulated rescuer to actually blow into the device to practice the actual technique that would be done in an emergency and fill an elastic balloon like receptacle that increases its internal pressure as it's inflated. This increase in pressure helps rescuers sense the feedback of inflating a live victim's lungs. Filling of the elastic receptacle also provides feedback to the victim to when to breathe in to raise their chest and provide feedback to the rescuer that their lungs are full. Practicing this way may help develop muscle memory in rescuers (e.g., lifeguards, first responders, etc.) to improve their training so in an actual emergency when CPR skills may be needed, the rescuer will not hesitate.

In operation, the second passageway of the split passageway resuscitation training device can be inserted into a CPR mask. Alternatively, in the second embodiment of the split passageway resuscitation training device, it can also receive a one-way CPR valve at the first passage way of the device. After the device has been coupled to the one-way valve, the CPR mask can be placed on a person acting as a victim. Once the CPR mask is in place, a person practicing using the CPR mask can begin using the split passageway resuscitation training device in combination with the CPR mask or CPR valve and CPR mask. Of note, as the person practicing giving breaths breathes into the combination, air from the person is directed out the side of the housing such that the person wearing the mask does not receive the breaths from the person practicing. The person wearing the mask can draw in breaths via the split passageway resuscitation training device and exhale via exhaust vents on the device, thus being able to breathe while the other person practices giving breaths.

Split Passageway Resuscitation Training Device

Referring to FIG. 1A through FIG. 1D, a plurality of different views of a first embodiment of a split passageway resuscitation training device 100 is illustrated. The first embodiment split passageway resuscitation training device 100 can typically be implemented with a CPR mask that does not include a one-way valve. The split passageway resuscitation training device 100 can be implemented to allow a user to practice giving breaths to a live person wearing a CPR mask.

Figure 1A:
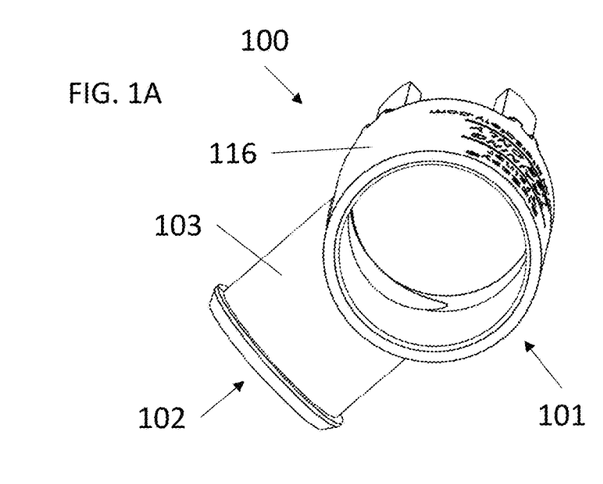
FIG. 1A through FIG. 1D include several different views of a split passageway resuscitation training device according to one embodiment of the present invention.
Figure 1B:
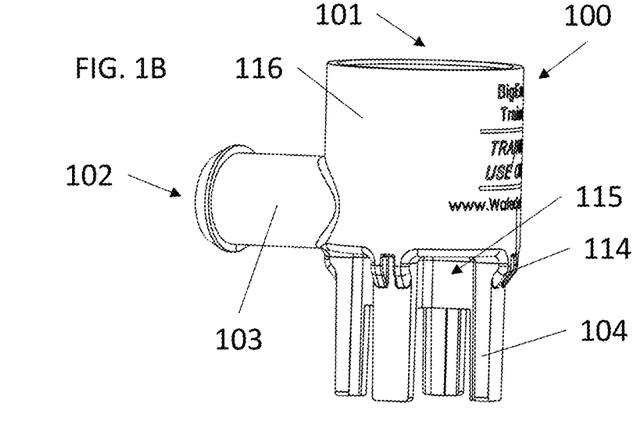
Figure 1C:
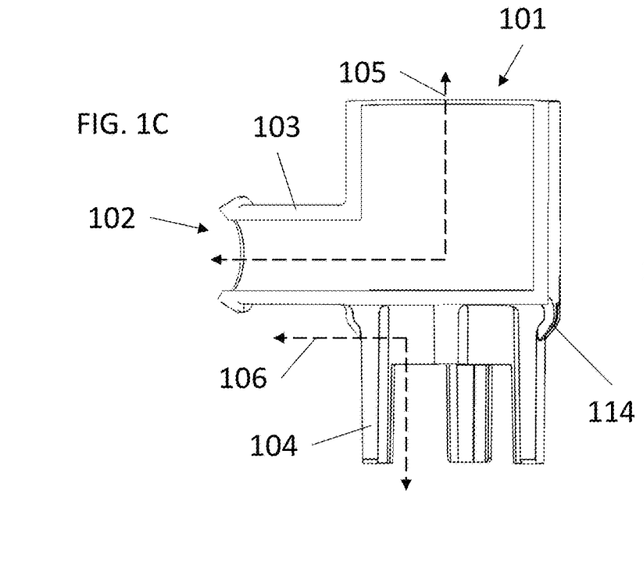
Figure 1D:
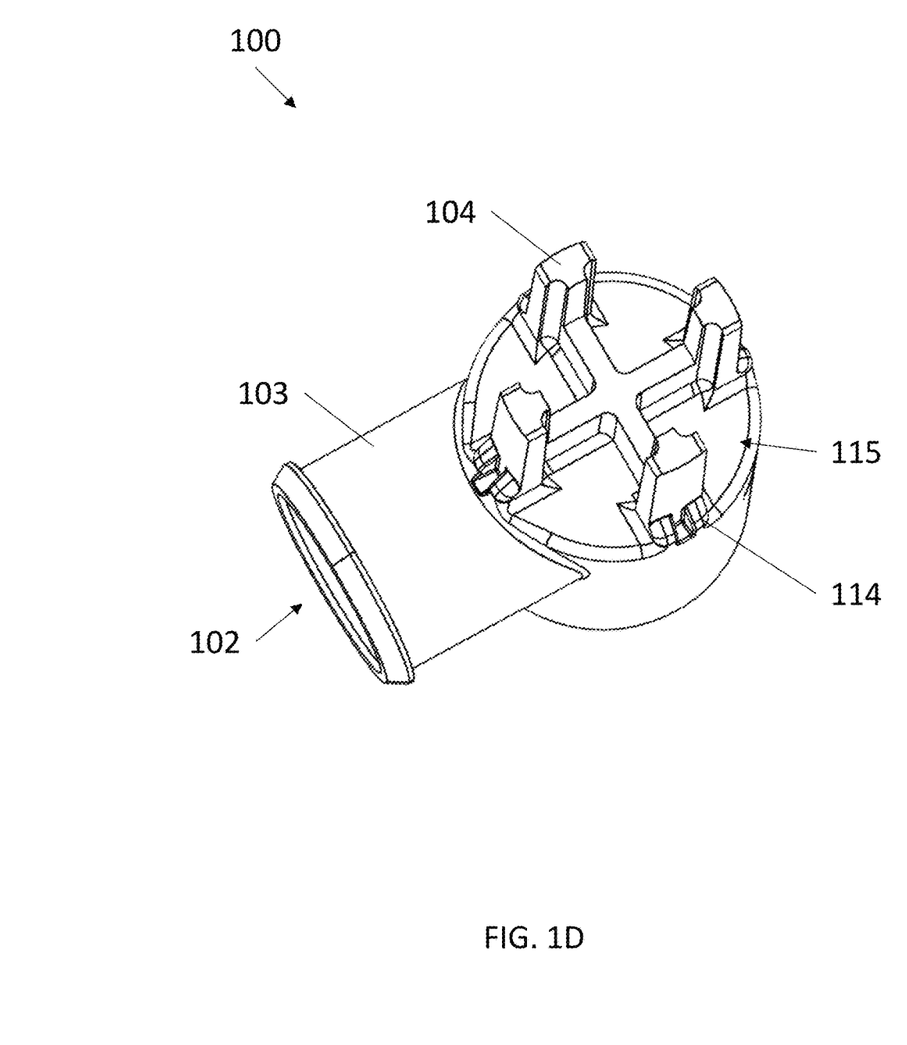

Referring to FIG. 1A, a top view of the split passageway resuscitation training device 100 is illustrated. Referring to FIG. 1B, a side view of the split passageway resuscitation training device 100 is illustrated. Referring to FIG. 1C, cross-sectional views of the split passageway resuscitation training device 100. Referring to FIG. 1D, a bottom perspective view of the split passageway resuscitation training device 100 is illustrated.

As shown generally in FIG. 1A through FIG. 1D, the split passageway resuscitation training device 100 can include, but is not limited to, a housing (or body) 116, a first passageway 105, a second passageway 106. Typically, each of the passageways 105, 106 can include an intake opening 101 and an exhaust opening 102. The passageways 105, 106 are shown via dotted lines in FIG. 1C.

Generally, the housing 116 can be sized and shaped to interact with a commonly available CPR mask, CPR valves and endotracheal tubes. As shown, the housing 116 can include a first passageway 105 and a second passageway 106. The first passageway 105 can be configured to be used by a rescuer and the second passageway 106 can be configured to be inserted into a CPR mask 108. External stops 114 limit the depth of insertion into the CPR mask to create breathing openings 115 for the victim. Of note, the second passageway 106 can be fluidly connected to the CPR mask such that a person whom has the mask on their face can breathe via the second passageway 106 through the openings 115.

As shown in FIG. 1C (via dotted lines), the housing 116 can separate the first passageway 105 and the second passageway 106. The first passageway 105 can be implemented to direct air blown into the passageway first opening 101 towards the second opening 102. The second passageway 106 creates a bidirectional breathing path between the CPR mask and the outside through opening 115.

As shown in FIG. 1D, the second passageway is created by a minimum of two legs 104 creating a discontinuous circular shape that can connect to generally available CPR masks with either the internal or external dimensions of the legs. External stops 114 limit the depth of insertion into the CPR mask to create breathing openings 115 for the victim.

Figure 2:
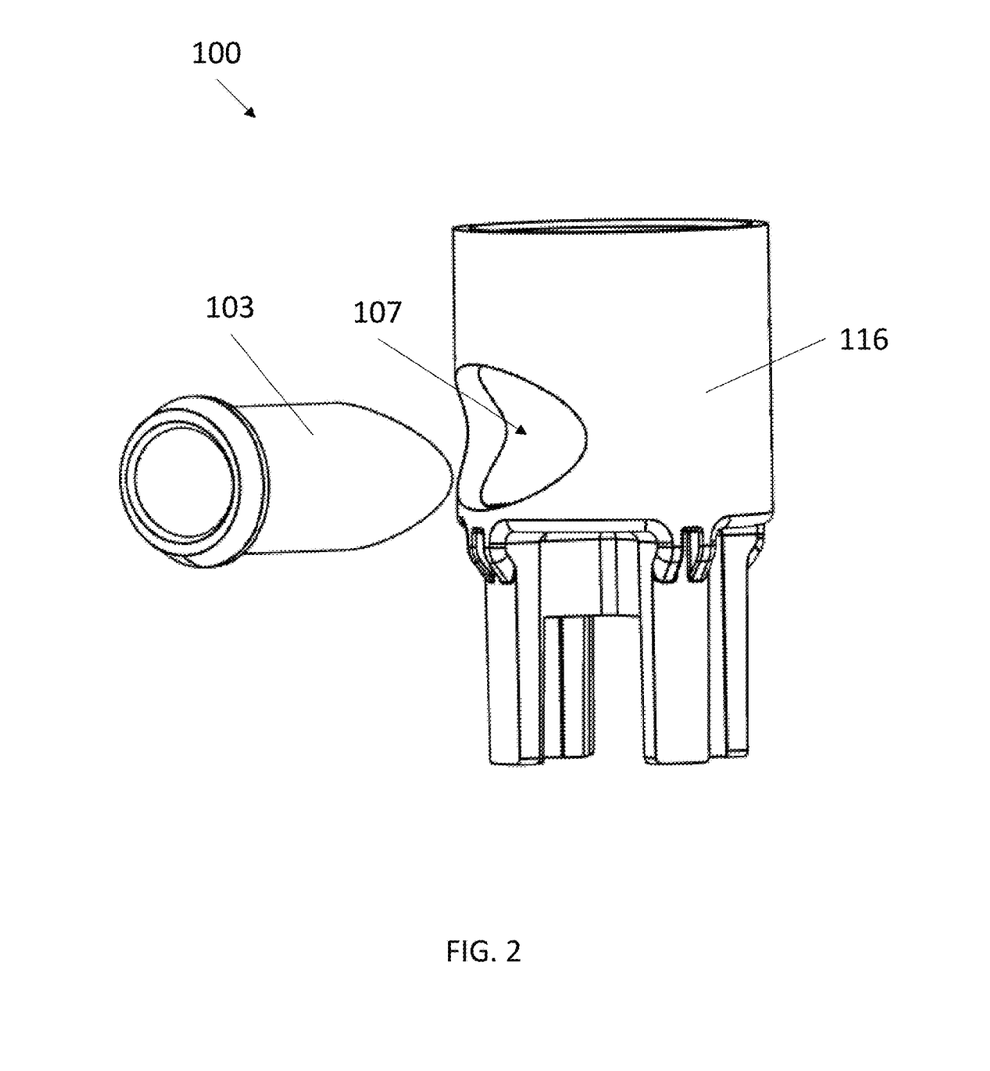
FIG. 2 is a perspective view of a split passageway resuscitation training device according to one embodiment of the present invention.

Referring to FIG. 2, the snout 103 of the split passageway resuscitation training device 100 can be removed from the housing 116 when an elastic balloon like receptacle is not being used to simulate lung inflation.

Figure 3A:
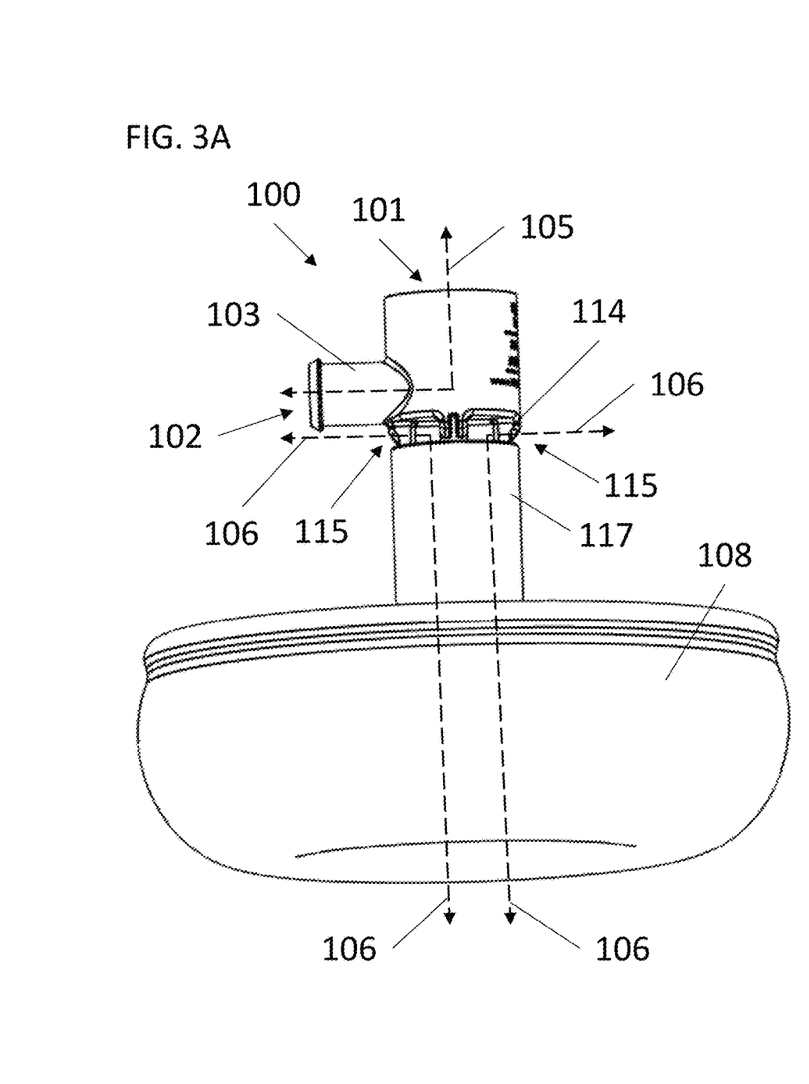
FIG. 3A is a perspective view of a split passageway resuscitation training device coupled to a CPR mask according to one embodiment of the present invention.

Referring to FIG. 3A, a detailed diagram of the split passageway resuscitation training device 100 coupled to a CPR mask 108 is illustrated. As shown, the legs 104 of the second portion of the housing 116 can be inserted into the entrance tube 117 of the CPR mask 108. Of note, the CPR mask 108 does not include a one-way valve. As previously mentioned, the first embodiment split passageway resuscitation training device 100 can typically be implemented with a CPR mask not including a one-way valve. As can be appreciated, the external stops 114 of the split passageway resuscitation training device limit the depth of insertion into the tube 117 and create multiple openings 115 for the simulated victim to breathe in and breathe out through second pathway 106 running from multiple openings 115 to a bottom opening of CPR mask 108.

Further shown in FIG. 3A is an airflow path through the passageways. Of note, a victim wearing the mask 108 can inhale and exhale via the second passageway 106. A rescuer practicing giving CPR to a victim may exhale breaths via the first passageway 105.

Figure 3B:
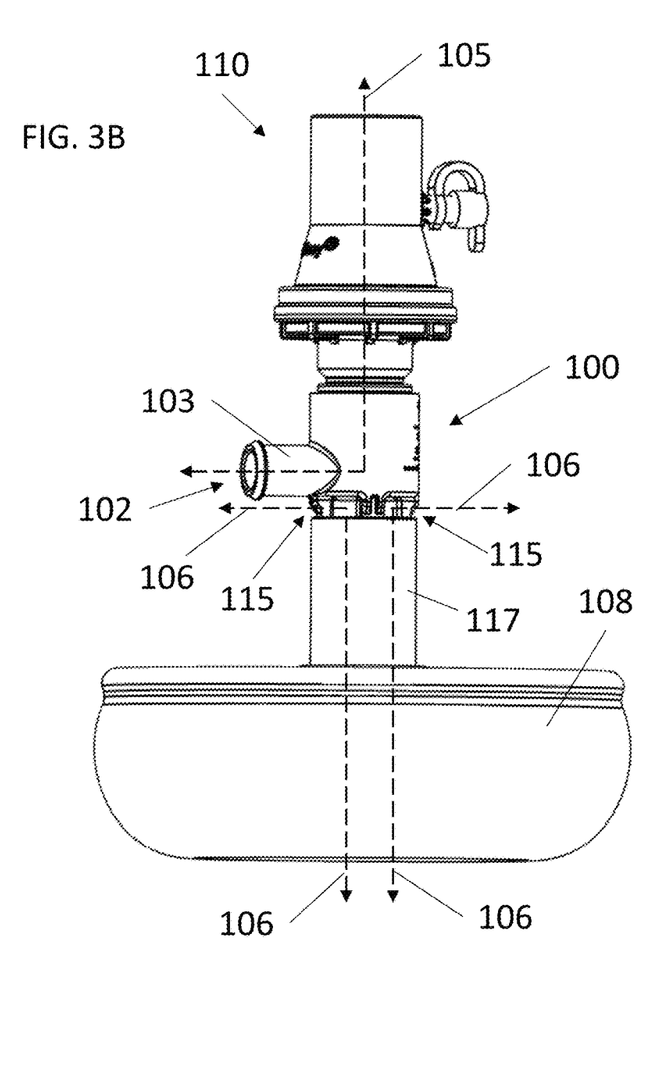
FIG. 3B is a perspective view of a split passageway resuscitation training device coupled to a CPR valve and CPR mask according to another embodiment of the present invention.

Referring to FIG. 3B, a detailed diagram of the split passageway resuscitation training device 100 coupled to a CPR mask 108 and CPR valve 110 is illustrated. As shown, the legs 104 of the second portion of the housing 116 can be inserted into the entrance tube 117 of the CPR mask 108. The CPR valve 110 is inserted into the intake opening 101 of the housing 116. As can be appreciated, the external stops 114 of the split passageway resuscitation training device limit the depth of insertion into the tube 117 and create multiple openings 115 for the simulated victim to breathe in and breathe out through second pathway 106 running from multiple openings 115 to a bottom opening of CPR mask 108.

Further shown in FIG. 3B are the airflow path through the passageways. Of note, a victim wearing the mask 108 can inhale and exhale via the second passageway 106. A rescuer practicing giving CPR to a victim may exhale breaths into the CPR valve 110, wherein exhaled breaths are directed to opening 102 in the first pathway snout 103 via the first passageway 105.

Figure 4A:
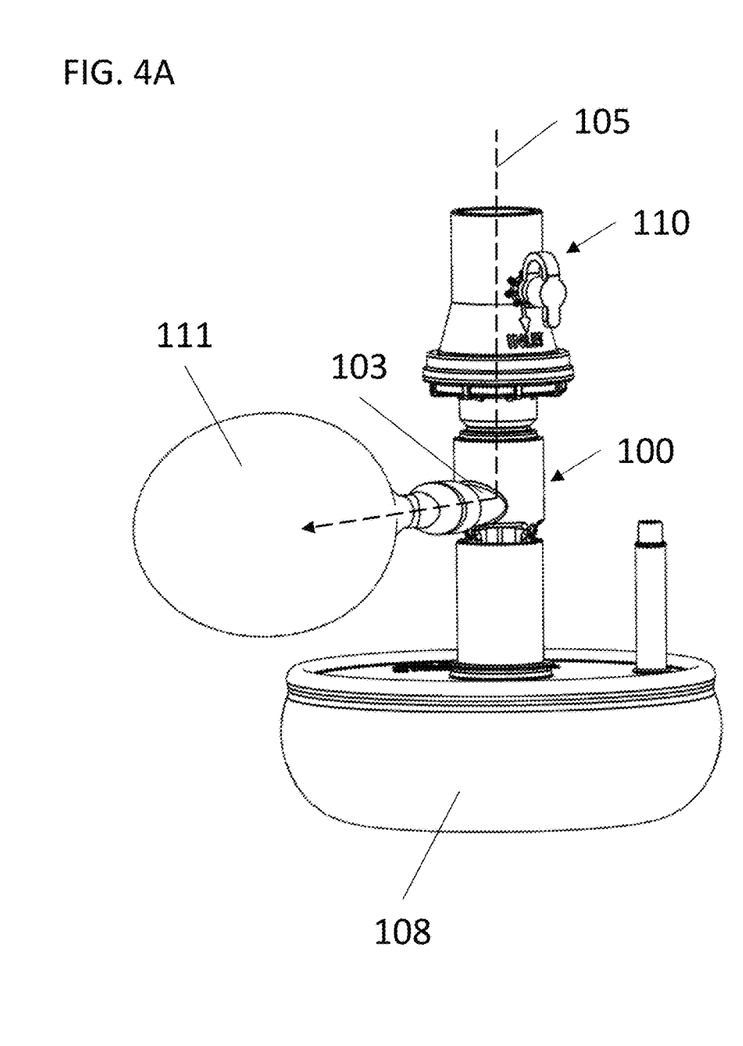
FIG. 4A is a perspective view of a split passageway resuscitation training device coupled to a CPR valve and CPR mask with an inflating elastic balloon during the rescuer's breathing into a CPR valve according to one embodiment of the present invention.

Referring to FIG. 4A, a detailed diagram of the split passageway resuscitation training device 100 coupled to a CPR mask 108 and CPR valve 110 is illustrated. Included is an elastic balloon receptacle 111 attached to snout 103 that has filled with air from a rescuer through the CPR valve 110, passing through passageway 105. The filling of the elastic receptacle 111 creates a pressure to simulate the inflation of a victim's lungs.

Figure 4B:
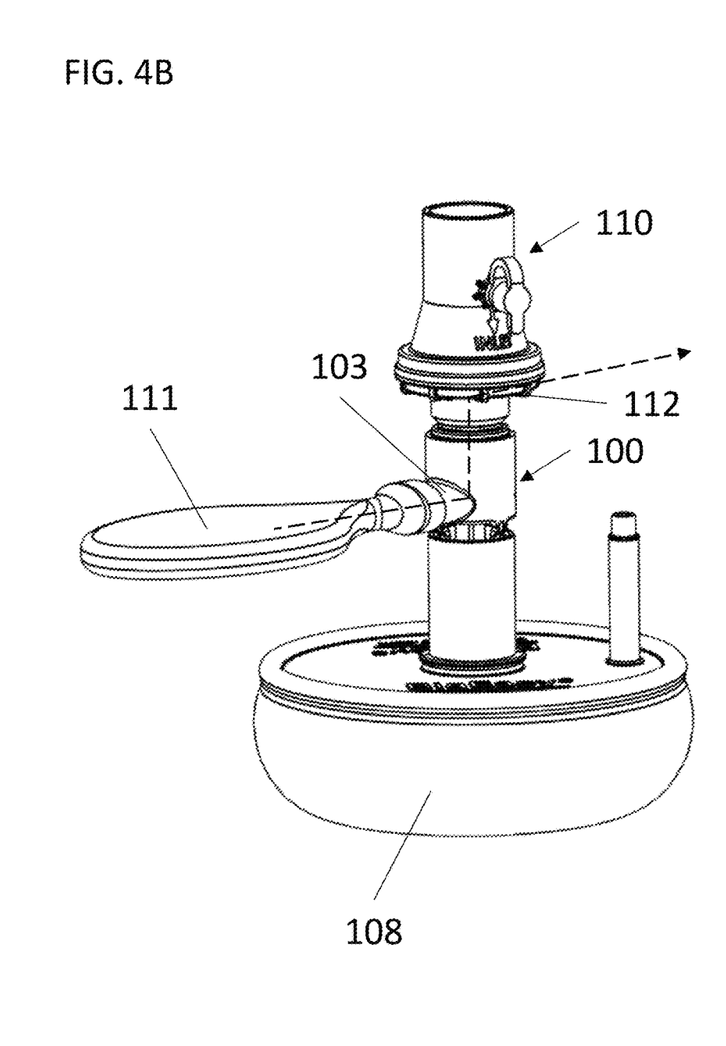
FIG. 4B is a perspective view of a split passageway resuscitation training device coupled to a CPR valve and CPR mask with a deflating elastic balloon during the simulated victim exhaling into a CPR valve according to one embodiment of the present invention.

Further shown in FIG. 4B a detailed diagram of the split passageway resuscitation training device 100 coupled to a CPR mask 108 and CPR valve 110 is illustrated. Included is an elastic balloon receptacle 111 attached to snout 103 that has emptied of air previously filled from a rescuer through the CPR valve 110, passing through passageway 105. The emptying of the elastic receptacle 111 passes the air through opening 102 to passageway 105 to the CPR valve 110 and exits the CPR valve though its exhalation openings 112.

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

What is claimed is:

1. A split passageway resuscitation training device comprising:
    a housing having a first portion and a second portion;
    wherein the first portion defines a first passageway extending between an upper first opening and a second opening positioned at an end of a laterally extending snout;
    wherein the second portion comprises at least two legs forming a discontinuous circular shape having an inner diameter and an outer diameter, the at least two legs each having an exterior physical stop extending outwardly past the outer diameter;
    wherein the first portion of the housing is adapted to interface with a source of resuscitation air and the second portion of the housing is adapted to interface with an entrance tube of a cardiopulmonary resuscitation (CPR) mask, such that only when the at least two legs are inserted into the entrance tube of the CPR mask and the exterior physical stops contact the entrance tube, a second passageway is formed between a plurality of side openings formed around the outer diameter between the exterior physical stops and a lower opening within the entrance tube of the CPR mask.

2. The device of claim 1, wherein the first opening of the first portion is a circular opening having a diameter between about 21 and 23 millimeters, and the second opening is located approximate to a middle portion of the housing.

3. The device of claim 1, wherein the outer diameter of the discontinuous circle formed by the at least two legs is between about 21 and 23 millimeters.

4. The device of claim 3, wherein the inner diameter of the discontinuous circle formed by the at least two legs is between about 14 and 16 millimeters.

5. The device of claim 1, wherein the first passageway is configured to channel a fluid entering from the first opening to exit from the second opening and to channel a fluid entering from the second opening to exit from the first opening.

6. The device of claim 1, wherein the second passageway is configured to channel a fluid entering from the plurality of side openings to exit from the lower opening and to channel a fluid entering from the lower opening to exit from the plurality of side openings.

7. The device of claim 1, further comprising an elastic balloon-like receptacle removably attached to the second opening of the first portion, wherein the receptacle is configured to collect a fluid flowing into the first opening of the first portion and to return the fluid to the first opening when a pressure at the second opening is greater than a pressure at the first opening.

8. The device of claim 1, wherein the snout is removably attached to the housing.

9. A split passageway resuscitation training device comprising:
    a housing having a first distal portion and a second proximal portion;
    wherein the first distal portion comprises:

a floor comprising a proximal surface and a distal surface; and a first passageway extending between an upper first opening at a distal end of the housing and a second opening positioned at an end of a laterally extending snout positioned between the distal end of the housing and the distal surface; and wherein the second proximal portion comprises:

a plurality of legs having a distal end and a proximal end and extending proximally from the proximal surface of the first distal portion, the plurality of legs forming a discontinuous circular shape having an inner diameter and an outer diameter; and a connector extending proximally from the proximal surface of the first distal portion and connecting the distal ends of the plurality of legs within the inner diameter;

wherein the plurality of legs are configured to engage an opening of an endotracheal tube to form a plurality of side openings between the endotracheal tube and the second proximal portion of the split passageway resuscitation training device.

10. The device of claim 9, wherein the first opening of the first distal portion is a circular opening having a diameter between about 21 and 23 millimeters, and the second opening is located approximate to a middle portion of the housing.

11. The device of claim 9, wherein the outer diameter of the discontinuous circle formed by the plurality of legs is between about 21 and 23 millimeters.

12. The device of claim 11, wherein the inner diameter of the discontinuous circle formed by the plurality of legs is between about 14 and 16 millimeters.

13. The device of claim 9, wherein the first passageway is configured to channel a fluid entering from the first opening to exit from the second opening and to channel a fluid entering from the second opening to exit from the first opening.

14. The device of claim 9, further comprising an elastic balloon-like receptacle removably attached to the second opening of the first distal portion, wherein the receptacle is configured to collect a fluid flowing into the first opening of the first distal portion and to return the fluid to the first opening when a pressure at the second opening is greater than a pressure at the first opening.

15. The device of claim 9, wherein the snout is removably attached to the housing.

16. A split passageway resuscitation training device comprising:

a housing having a first distal portion and a second proximal portion;

wherein the first distal portion comprises:

a floor comprising a proximal surface and a distal surface; and a first passageway extending between an upper first opening at a distal end of the housing and a second opening positioned at an end of a laterally extending snout positioned between the distal end of the housing and the distal surface; and wherein the second proximal portion comprises:

a plurality of legs having a distal end and a proximal end and extending proximally from the proximal surface of the first distal portion, the plurality of legs forming a discontinuous circular shape having an inner diameter and an outer diameter;

an exterior physical stop extending outwardly from the distal end of each leg past the outer diameter; and a connector extending proximally from the proximal surface of the first distal portion and connecting the distal ends of the plurality of legs within the inner diameter.

17. The device of claim 16, wherein the outer diameter of the discontinuous circular shape formed by the plurality of legs is between about 21 and 23 millimeters.

18. The device of claim 17, wherein the inner diameter of the discontinuous circular shape formed by the plurality of legs is between about 14 and 16 millimeters.

* * * * *